(12) United States Patent
Knuchel et al.

(10) Patent No.: US 8,057,474 B2
(45) Date of Patent: Nov. 15, 2011

(54) TELESCOPIC STRUT FOR AN EXTERNAL FIXATOR

(75) Inventors: Beat Knuchel, Ursenbach (CH);
Vinzenz Burgherr, Wabern (CH);
Christian Steiner, Eisenach (DE);
Meinrad Fiechter, Münsingen (CH)

(73) Assignee: Stryker Trauma SA (CH)

( * ) Notice: Subject to any disclaimer, the term of this patent is extended or adjusted under 35 U.S.C. 154(b) by 467 days.

(21) Appl. No.: 12/286,100

(22) Filed: Sep. 26, 2008

(65) Prior Publication Data

US 2009/0198234 A1 Aug. 6, 2009

(30) Foreign Application Priority Data

Feb. 1, 2008 (EP) ..................................... 08150960

(51) Int. Cl.
*A61F 5/04* (2006.01)
(52) U.S. Cl. ............... 606/57; 606/54; 606/55; 606/56; 606/58; 606/258; 606/86 R; 606/259
(58) Field of Classification Search .............. 606/54–59, 606/258, 259, 86 R
See application file for complete search history.

(56) References Cited

U.S. PATENT DOCUMENTS

| | | | |
|---|---|---|---|
| 2,291,747 A | 8/1942 | Neuwirth | |
| 2,883,219 A | 4/1959 | Cox | |
| 3,691,788 A | 9/1972 | Mazziotti | |
| 3,977,397 A | 8/1976 | Kalnberz et al. | |
| 4,308,863 A | 1/1982 | Fischer | |
| 4,365,624 A | 12/1982 | Jaquet et al. | |
| 4,520,983 A | 6/1985 | Templeman | |
| 4,554,915 A | 11/1985 | Brumfield | |
| 4,615,338 A | 10/1986 | Ilizarov et al. | |
| 4,768,524 A | 9/1988 | Hardy et al. | |
| 4,819,496 A | 4/1989 | Shelef | |
| 4,978,348 A | 12/1990 | Ilizarov | |
| 5,028,180 A | 7/1991 | Sheldon et al. | |
| 5,087,258 A | 2/1992 | Schewior | |

(Continued)

FOREIGN PATENT DOCUMENTS

DE 202006006734 U1 6/2006

(Continued)

OTHER PUBLICATIONS

European Search Report, EP 08 15 0960.

(Continued)

*Primary Examiner* — Eduardo C Robert
*Assistant Examiner* — Ellen C Hammond
(74) *Attorney, Agent, or Firm* — Lerner, David, Littenberg, Krumholz & Mentlik, LLP

(57) ABSTRACT

A telescopic strut for use with an external fixator includes a tube and a rod, especially a threaded rod being in threaded engagement with the tube. The tube comprises at least one hole for accommodating a ball, the ball having the spherical shape for engagement with the threaded rod. A sleeve is provided on the portion of the tube comprising the hole. The sleeve comprises a non-spherical inner cross-section. The greater diameter of the sleeve has a dimension which is at least the sum of the outer diameter of the threaded rod plus the diameter of an accommodating ball for allowing direct axial movement of the threaded rod against the tube in such a rotational position of the sleeve. The lesser diameter has a dimension to place the ball within the threaded rod for allowing a rotational movement of the threaded rod against the tube.

15 Claims, 4 Drawing Sheets

U.S. PATENT DOCUMENTS

| | | | |
|---|---|---|---|
| 5,358,504 | A | 10/1994 | Paley et al. |
| 5,466,237 | A | 11/1995 | Byrd, III et al. |
| 5,702,389 | A | 12/1997 | Taylor et al. |
| 5,709,681 | A | 1/1998 | Pennig et al. |
| 5,728,095 | A | 3/1998 | Taylor et al. |
| 5,863,292 | A | 1/1999 | Tosic |
| 5,870,834 | A | 2/1999 | Sheldon |
| 5,971,984 | A | 10/1999 | Taylor et al. |
| 6,021,579 | A | 2/2000 | Schimmels et al. |
| 6,030,386 | A * | 2/2000 | Taylor et al. .......... 606/56 |
| 6,090,111 | A | 7/2000 | Nichols |
| 6,176,860 | B1 | 1/2001 | Howard |
| 6,371,957 | B1 | 4/2002 | Amrein et al. |
| 6,565,565 | B1 | 5/2003 | Yuan et al. |
| 6,565,567 | B1 | 5/2003 | Haider |
| 6,671,975 | B2 | 1/2004 | Hennessey |
| 6,701,174 | B1 | 3/2004 | Krause et al. |
| 6,733,502 | B2 | 5/2004 | Altarac et al. |
| 6,769,194 | B2 | 8/2004 | Hennessey |
| 7,022,122 | B2 | 4/2006 | Amrein et al. |
| 7,197,806 | B2 | 4/2007 | Boudreaux et al. |
| 7,282,052 | B2 | 10/2007 | Mullaney |
| 7,306,601 | B2 | 12/2007 | McGrath et al. |
| 7,377,923 | B2 | 5/2008 | Purcell et al. |
| 7,422,593 | B2 | 9/2008 | Cresina et al. |
| 2001/0025181 | A1 | 9/2001 | Freedlan |
| 2002/0010465 | A1 | 1/2002 | Koo et al. |
| 2003/0063949 | A1 | 4/2003 | Hohenocker |
| 2005/0015087 | A1 | 1/2005 | Walulik et al. |
| 2005/0084325 | A1 | 4/2005 | O'Brien et al. |
| 2005/0248156 | A1 | 11/2005 | Hsieh |
| 2005/0251136 | A1 | 11/2005 | Noon et al. |
| 2006/0184169 | A1 | 8/2006 | Stevens |
| 2006/0243873 | A1 | 11/2006 | Carnevali |
| 2006/0247622 | A1 | 11/2006 | Maughan et al. |
| 2006/0247629 | A1 | 11/2006 | Maughan et al. |
| 2006/0261221 | A1 | 11/2006 | Carnevali |
| 2007/0055234 | A1 | 3/2007 | McGrath et al. |
| 2007/0161984 | A1 | 7/2007 | Cresina et al. |
| 2007/0162022 | A1 | 7/2007 | Zhang et al. |
| 2007/0250071 | A1 | 10/2007 | Soerensen et al. |
| 2008/0021451 | A1 | 1/2008 | Coull et al. |
| 2009/0198235 | A1 | 8/2009 | Steiner et al. |
| 2010/0087819 | A1 | 4/2010 | Mullaney |

FOREIGN PATENT DOCUMENTS

| | | |
|---|---|---|
| EP | 0377744 A1 | 7/1990 |
| EP | 1016381 | 12/2003 |
| FR | 2439002 | 5/1980 |
| FR | 2576774 A1 | 8/1986 |
| FR | 2756025 A1 | 5/1998 |
| IT | 1259768 B | 3/1996 |
| WO | 01/15611 | 3/2001 |
| WO | 01/78613 | 10/2001 |
| WO | 03/086213 | 10/2003 |

OTHER PUBLICATIONS

Smith&Nephew, Taylor Spatial Frame, website printout, Aug. 12, 2009.

Alizade et al., Mech. Mach. Theory, vol. 29, No. 1, pp. 115-124, 1994, Great Britain.

International Search Report and Written Opinion, PCT/US2010/000712, dated Jun. 28, 2010.

European Search Report, EP 08 15 0944.

European Search Report, EP 08 15 0971.

European Search Report EP 09 15 0507.

* cited by examiner

TELESCOPIC STRUT FOR AN EXTERNAL FIXATOR

BACKGROUND OF THE INVENTION

The invention relates to a telescopic strut for an external fixator, especially for use with an external ring fixator.

A plurality of compression-distraction apparatus have been designed and improved by Ilizarov and his group using two external rings to be placed around the limb to be fixed. There are usually at least two such rings, one proximal and one distal ring, which are connected with a plurality of struts or rods. Preferably, these struts are linked to the rings in a way that the attachment points can be pivoted and the length of the strut can be varied to enable adjustment of the external fixation rings.

Ilizarov has also provided some improvements for said systems. EP 0 377 744 shows a telescopic strut for such an external fixator. U.S. Pat. No. 4,615,338 shows a further device to control the length of such telescopic struts.

A different external ring fixator having telescopic struts is shown in U.S. Pat. No. 5,702,389.

SUMMARY OF THE INVENTION

However, these devices, which can be used to shorten or lengthen the telescopic struts, are difficult to adjust and it is one object of the invention to improve the ease of adjusting the length of the rod.

Based on the prior art, it is therefore an object of the invention to provide a telescopic strut, which can be readily and quickly changed in its length.

It is another aspect of the invention, to allow, as an alternative, fine adjustments of the struts.

In view of the above mentioned aspect it is furthermore another aspect of the invention to allow a quick switch between the two functions, i.e. to allow a quick first definition of the length of the telescopic element, and additionally, to switch for a fine adjustment of said length.

BRIEF DESCRIPTION OF THE DRAWINGS

The invention is now described with reference to the enclosed drawings, showing preferred embodiments of the telescopic strut.

DETAILED DESCRIPTION

Figure 1:
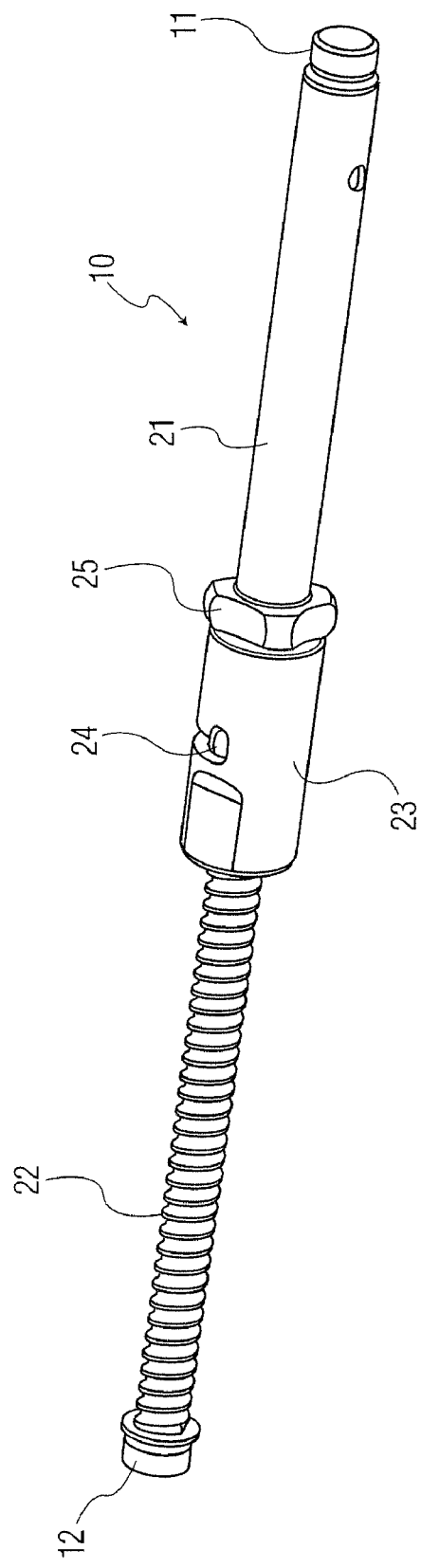
FIG. 1 is a perspective view of a telescopic strut according to the invention.

Referring to FIG. 1 there is shown a perspective view of a telescopic strut according to the invention generally denoted as 10. The telescopic strut comprises two free ends 11 and 12 being attachment points for connecting the rod with two external rings to be placed around the limb to be fixed. The attachment points 11 and 12 according to this embodiment comprise cylindrical knobs, but this entirely depends on the kind of fixation element for which the rod is used.

Figure 2:
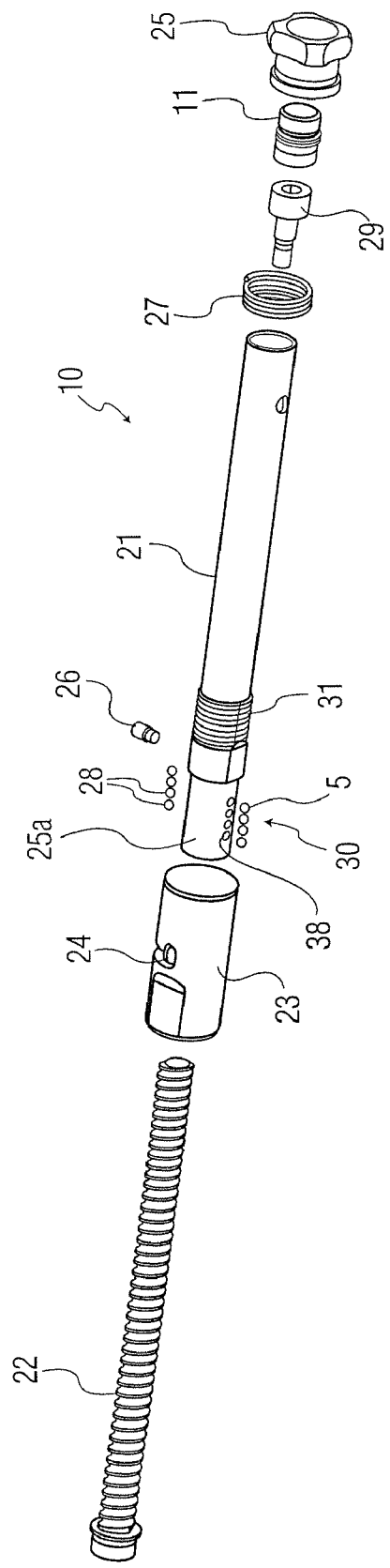
FIG. 2 is an exploded view of the telescopic strut according to FIG. 1.

FIG. 1 shows the main components of the telescopic strut. There is an outer tube 21 in which the threaded rod 22 is partially located. The opposite thread element 30 is located within the sleeve 23 and is better seen in FIG. 2 as well as FIG. 3 and will be described below and comprises balls 28 which ride in the threads of rod 22. In the preferred embodiment sleeve 23 comprises a bayonet groove 24 for a quick change between the desired quick length change mode and the fine adjustment mode. The sleeve 23 can be switched between two rotational positions for this, i.e. to lock and unlock the axial direction. Therefore the groove 24 has a U-form, the ends of the groove 24 defining the two positions with the help of a bolt 26 fixedly mounted on outer tube 21 provided within the groove 24. The ends of the groove 24 are oriented in axial direction of the telescopic strut. The ends show in the same direction, towards the spring 27 as can be seen in the exploded view of FIG. 2, to allow displacement of the bolt 26 against the force of spring 27.

A security mechanism, to avoid unintentional switching, is realized by an additional nut 25 which engages a thread 31 on an outer surface of tube 21, blocking the bolt 26 in one of the free ends of groove 24.

Figure 3:
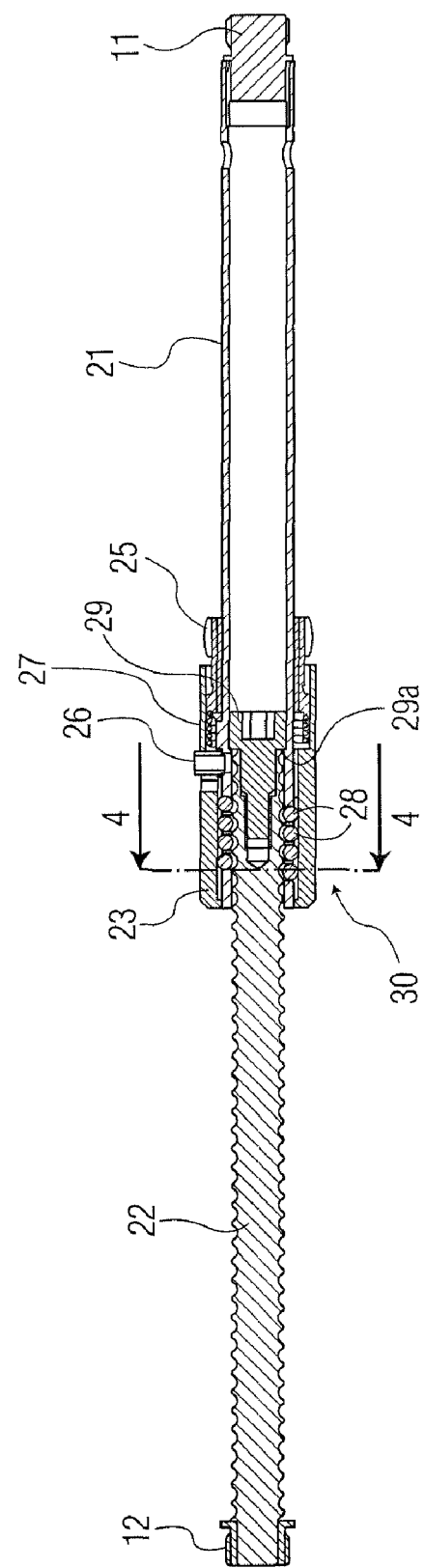
FIG. 3 is a side view in cross-section of the telescopic strut according to FIG. 1.

FIG. 3 shows a view in cross-section of the telescopic strut according to FIG. 1. Sleeve 23 can be pushed against action of spring 27 provided on the outer tube 21 and which spring is biased with help of nut 25. Then the sleeve 23 is turned around 90° and is arrested within the other free end of the groove 24. It is preferred that this position is fixed through nut 25.

The turning angle of 90 degrees is defined in view of the way the quick length adjustment mode is working. This can be seen in FIG. 4 being a representation of a cross section of the rod along line III-III in FIG. 3. It can be seen from FIG. 4 that the sleeve 23 has a non-cylindrical inner bore. The bore can be e.g. elliptical. The shorter diameter of the bore is sufficient to accommodate the outer diameter of the foremost portion 25a of outer tube 21, which is cylindrical. Foremost portion 25a comprises on both sides a plurality of preferably, four holes 38 to accommodate one ball 28 each. Of course, it is also possible to provide only two balls on each side or five or more. Three or four balls have been proven to be sufficient without lengthening the sleeve 23 too much.

Figure 4:
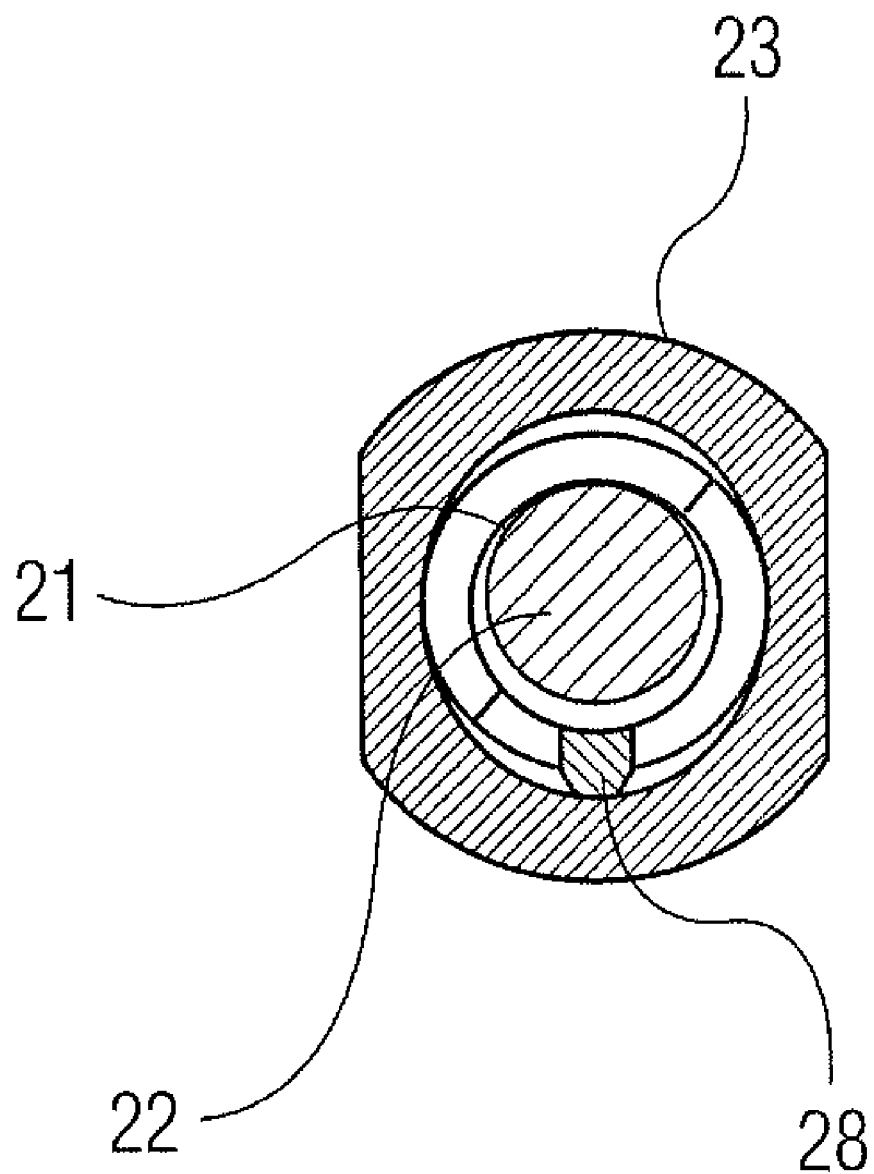
FIG. 4 is a cross section of the rod along line III-III in FIG. 3.

The inner diameter of outer tube 21 is greater than the outer thread portion of the rod 22 which is cylindrical. Therefore, the rod 22 can be pushed into the outer tube 21, when the bolt 26 is in a position which allows the sleeve 23 to be oriented as shown in FIG. 4. Then the balls 28 can freely move against the inner wall of sleeve 23 and the rod 22 can be axially pushed. For that the sum of the outer diameter of the rod 22 and twice the diameter of the balls 28 is less or nearly equal to the inner diameter of the sleeve 23.

It is avoided that the threaded rod 22 can be separated from the outer tube 21 through an abutment screw 29 which is screwed into a corresponding thread within the threaded rod 22 and which can abut on a corresponding shoulder 29a within the tube 21 as shown in FIG. 3.

By turning the sleeve 23 around the bolt 26, i.e. by 90°, the balls 28 will be moved because of the elliptic inner shape within the sleeve 23. In this way the balls 28 are pushed through holes 38 towards the grooves of the thread 22 for interlocking, i.e. connecting the thread with the outer tube 21, because the balls 28 stand within both parts and leave no room to allow a direct axial movement of the threaded rod 22.

In this position the threaded rod 22 still can be moved axially through rotational movement of tube 21 being directly coupled via bolt 26 to sleeve 23 against the threaded rod 22 which can rotate in view of the balls 28 pressed in its threads. This allows the fine adjustment.

Thus the elements allow for a quick change between free axial adjustment of the telescopic strut, if the balls 28 do not engage the threaded rod 22. If the balls do engage rod 22 then a fine adjustment through rotation of the outer tube 21/rod 22 is allowed. The balls 28 are engaging the one or subsequent grooves of the threaded rod 22, e.g. depending on the pitch of the rod. The pitch angle of the thread can be chosen e.g. between 30 and 60 degrees and especially between 40 and 50 degrees.

It is clear that this fine adjustment is only possible, if at least one free end 11 or 12 of the telescopic strut can be rotated while fixed within an external fixator ring.

Within another embodiment (not shown) a helically threaded rod is replaced by a rod having a plurality of radial grooves. Each of these grooves has dimensions to accommodate one of the balls 28. In other words, the threaded rod having a groove providing a pitch is replaced by a sequence of separated adjacent radial grooves. It is thus possible to use such a rod with a flank lead to block the device in a plurality of positions. However, with radial grooves it is not possible to allow a fine tuning through rotation of tube 21.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A telescopic strut for use with an external fixator, comprising
   a tube,
   a rod rotatably mounted in a bore of said tube, and
   a sleeve provided on the tube;
   wherein the tube comprises a portion with at least one hole for accommodating a ball;
   wherein the rod comprises at least one groove;
   wherein the ball has the spherical dimension for engagement with said groove of the rod;
   wherein the sleeve is provided on the portion of the tube having the hole, wherein the sleeve comprises a non-cylindrical inner cross-section, wherein the greater diameter of the sleeve has a dimension which is at least the sum of an outer diameter of the rod plus a diameter of the accommodated ball for allowing direct axial movement of the rod against the tube in such a rotational position of the sleeve, while the lesser diameter has a dimension to accommodate the ball within the groove of the rod.

2. The telescopic strut according to claim 1, wherein the rod has at least one groove forming a threaded rod, wherein the at least one groove of the rod provides for an engagement with the ball accommodated within said tube, wherein the ball has spherical dimension for engagement with the groove of the threaded rod, wherein the sleeve has an elliptical inner bore wherein a lesser diameter of the sleeve inner bore has a dimension to accommodate the ball within the threaded rod groove for allowing a rotational movement of the threaded rod against the tube.

3. The telescopic strut according to claim 2, wherein at least one of the free opposite ends of the tube comprises the rotatable sleeve for allowing fine adjustment of the length of the rod through rotation of the threaded rod against the outer tube.

4. The telescopic strut according to claim 2, wherein at least one of the free opposite ends of the rod comprises the rotatable sleeve for allowing fine adjustment of the length of the rod through rotation of the threaded rod against the outer tube.

5. The telescopic strut according to claim 1, wherein the tube comprises a plurality of holes at positions surrounded by the sleeve and wherein the sleeve has a central bore having an elliptical cross section and in that the greater diameter of the sleeve central bore has a dimension which is at least the sum of the outer diameter of the rod plus twice the diameter of the accommodating balls.

6. The telescopic strut according to claim 1, wherein the rotatable sleeve comprises a U-shaped groove, wherein the free ends of the U-shape are directed against a spring, to bias the sleeve with the help of a bolt being fixed within the outer tube.

7. The telescopic strut according to claim 6, wherein the movement of the sleeve against the spring can be blocked by a nut being in threaded relationship with the tube.

8. The telescopic strut according to claim 6, wherein the two arms of the U-shaped groove are oriented parallel in an angle of 90° apart, to allow fixation of the sleeve in two separate positions.

9. The telescopic strut according to claim 8, wherein the movement of the rotatable sleeve can be blocked by a nut being in threaded relationship with tube.

10. A telescopic strut for use with an external fixator comprising:
    an axially extending rod having a series of circumferential grooves on an outer surface of the rod;
    an axially extending tube for receiving the rod, the tube having a leading end including a plurality of holes formed in a wall of the tube;
    a plurality of balls for extending through the holes in the leading end;
    a sleeve having an eccentric bore therethrough mounted around the tube leading end for contacting the balls, the bore having a major diameter allowing the balls to be located outside the grooves of the rod and a minor diameter causing the balls to be held within the grooves on the rod.

11. The telescopic strut as set forth in claim 10 further comprising a means for holding the sleeve in a first position where the major diameter engages the balls or a second position where the minor diameter engages the balls.

12. The telescopic strut as set forth in claim 11 wherein the means includes a spring biasing the sleeve towards the second position.

13. The telescopic strut as set forth in claim 10 wherein the grooves in the rod are formed by a helical thread extending along the axial extent thereof.

14. The telescopic strut as set forth in claim 10 wherein the grooves are formed by a plurality of radial ridges.

15. The telescopic strut as set forth in claim 10 wherein the balls are at least partially retained within the holes of the leading end when contacted by the minor diameter of the sleeve.

* * * * *